USOO5626617A

United States Patent [19]
Brewitt

[11] Patent Number: 5,626,617
[45] Date of Patent: May 6, 1997

[54] METHODS FOR TREATING DISORDERS BY ADMINISTERING RADIO FREQUENCY SIGNALS CORRESPONDING TO GROWTH FACTORS

[76] Inventor: Barbara Brewitt, 6812 Woodlawn Ave. NE., Seattle, Wash. 98115-5420

[21] Appl. No.: 575,840

[22] Filed: Dec. 20, 1995

Related U.S. Application Data

[63] Continuation of Ser. No. 221,365, Mar. 31, 1994, abandoned.

[51] Int. Cl.$^6$ ................................................. A61M 39/00
[52] U.S. Cl. ............................ 607/2; 128/898; 604/20; 601/15
[58] Field of Search ........................ 128/898, 903; 607/2; 601/15; 604/19-22

[56] References Cited

U.S. PATENT DOCUMENTS

| | | | |
|---|---|---|---|
| 4,341,762 | 7/1982 | Haast | 424/88 |
| 4,828,830 | 5/1989 | Wong | 424/85.5 |
| 4,863,902 | 9/1989 | Amagase et al. | 514/12 |
| 4,886,747 | 12/1989 | Derynck et al. | 435/69.4 |
| 4,989,604 | 2/1991 | Fang | 607/2 |
| 5,000,178 | 3/1991 | Griffith | 607/2 |
| 5,108,989 | 4/1992 | Amento et al. | 514/12 |
| 5,118,791 | 6/1992 | Burnier et al. | 530/326 |
| 5,168,051 | 12/1992 | Derynck et al. | 435/69.4 |
| 5,231,988 | 8/1993 | Wernicke et al. | 607/2 |

FOREIGN PATENT DOCUMENTS

| | | | |
|---|---|---|---|
| 2418646 | 9/1979 | France | 607/2 |
| 797686 | 1/1981 | U.S.S.R. | 607/2 |
| 1538916 | 1/1986 | U.S.S.R. | |
| 1289491 | 2/1987 | U.S.S.R. | 607/2 |
| 1538916 | 1/1990 | U.S.S.R. | 607/2 |
| 2128093 | 4/1984 | United Kingdom | 607/2 |
| 2T51489 | 7/1985 | United Kingdom | |
| 2151489 | 7/1985 | United Kingdom | 607/2 |

OTHER PUBLICATIONS

The Life Information System TEN, Listen for the Information Age, BIOSOURCE, Incorporated.

Garcia-Blanco, M.A., and Cullen, B.R., Molecular Basis of Latency in Pathogenic Human Viruses, Science 254:815-820, 1991.

Fey, S.J., and Larsen, P.M., DNA Viruses and Human Cancer, Cancer Letters 41:1-18, 1988.

Thomas, J.R. et al., Low-Intensity Magnetic Fields Alter Operant Behavior in Rats, Bioelectromagnetics 7:349-357, 1986.

Kleijnen, J. et al., Clinical Trials of Homeopathy, Brit. Med. J. 302:316-323, 1991.

Voll, Reinhold, The Phenomenon of Medicine Testing in Electroacupuncture According to Voll, Am. J. Acupuncture, vol. 8, No. 2, 97-104, Apr.-Jun. 1990.

Bergsmann et al., Differences in Electrical Skin Conductivity Between Acupuncture Points & Adjacent Skin Areas, Am. J. Acupuncture, 1:27-32, 1973.

Phillips et al., Magnetic field-induced changes in specific gene transcription Biochemica et Biophysica Acta, 1132:140-144, 1992.

American Heritage Dictionary (1982) pp. 77 and 272.

Cecil, *Textbook of Medicine* (1979) pp. 1650-1656; 1661-1663.

(List continued on next page.)

*Primary Examiner*—Robert A. Hafer
*Assistant Examiner*—Chalin Smith
*Attorney, Agent, or Firm*—Ann W. Speckman; Janet Sleath

[57] ABSTRACT

The present invention comprises homeopathic dilutions of growth factors and methods for their use. Disorders which may be effectively treated with the compositions of the present invention include chronic viral disorders, such as HIV, AIDS, chronic fatigue syndrome and Epstein-Barr viral infections, cancer and diabetes. Homeopathic dilutions of growth factors are preferably administered orally. In an alternative embodiment, patients are treated with electromagnetic signals, preferably radiofrequency signals, corresponding to homeopathic dilutions of growth factors.

18 Claims, 10 Drawing Sheets

OTHER PUBLICATIONS

McDonald et al., A Structural Superfamily of Growth Factors Containing a Cystine Knot Motif, Cell, vol. 73, pp. 421–424, May 7, 1993.

Ives, A Strategy for Research in Homeopathy, British Homeopathic Journal, vol. 72, No. 4, pp. 225–229, Oct. 1983.

Turner, Is There a Bridge Between Homeopathy and Conventional Medicine, British Homeopathic Journal, vol. 78, pp. 230–236, Oct. 1989.

Harisch et al., Smallest Zinc Quantities Affect the Histamine Release from Peritoneal Mast Cells of the Rat, Experientia, vol. 44, pp. 761–762, 1988.

Davenas et al., Explanation of Benveniste, Nature, vol. 334, pp. 285–291, 28 Jul. 1988.

Davenas et al., Human Basophil Degranulation Triggered by Very Dilute Antiserum Against IgE, Nature, vol. 333, pp. 816–818, 30 Jun. 1988.

Smith et al., Modern Instrumentation for the Evaluation of Homeopathic Drug Structure, Journ of Amn. Inst. of Homeopathy, Sep./Oct., pp. 263–278, 1966.

Kleijnen et al., Clinical Trials of Homeopathy, British Medical Journal, pp. 323–326, Feb. 9, 1991.

Scofield, Experimental Research in Homeopathy—a Critical Review (Conclusion) British Homeopathic Journal, vol. 73., No. 4, pp. 211–226, Oct. 1984.

Sorrentino, Growth Factors, Growth Inhibitors and Cell Cycle Control, Anticancer Research, vol. 9, pp. 1925–1936, 1989.

Gárcio–Blanco et al, Molecular Basis of Latency in Pathogenic Human Viruses, Science, vol. 254, pp. 815–820, 8 Nov. 1991.

Thomas et al., Low Intensity Magnetic Fields Alter Operant Behavior in Rats, Bioelectromagnetics, vol. 7, pp. 349–357, 1986.

Sersa et al., Inhibition of SA–1 Tumor Growth in Mice by Human Leukocyte Interferon Alpha Combined with Low-–Level Direct Current, Molecular Biology, vol. 2, pp. 165–168, 1990.

Tsuchitani et al., Potentiation of Cytotoxicity Against Human Ovarian Cell–Lines with Combinations of Subtoxic Concentrations of Tumor Necrosis Factor and Adriamycin or Cisplatinum, J.Cell Pharmacol., vol. 2, pp. 1–11, 1991.

The history of electrodermal screening and the Listen device, *excerpts from the Computerized Electro Dermal Screening & the Life Information System TEN manual*, pp. 21–27, 1991.

A Discussion of Research with Bibliography, *excerpts from the Computerized Electro Dermal Screening & the Life Information System TEN manual*, pp. 2–28, 1991.

Information concerning the Products Library and Databases Library, *excerpts from the Computerized Electro Dermal Screening & the Life Information System TEN manual*, pp. 39–40, 1994.

Dr. David A. Siegel, Bioenergetic Testing: the Listen System, Siegel Chiropractic Center.

Declaration of Dr. Barbara Brewitt outlining her research with the Listen system, and specifically, the use of radio frequency signals corresponding to growth factors in the treatment of chronic viral disorders.

METHODS FOR TREATING DISORDERS BY ADMINISTERING RADIO FREQUENCY SIGNALS CORRESPONDING TO GROWTH FACTORS

This application is a continuation of U.S. patent application No. 08/221,365, filed on Mar. 31, 1994, now abandoned.

FIELD OF THE INVENTION

This invention relates to the treatment of disorders such as chronic viral infections, cancer and diabetes and more particularly to the use of homeopathic dilutions of growth factors to treat such disorders.

BACKGROUND OF THE INVENTION

One aspect of this invention relates to the treatment of chronic viral infections by administration of homeopathic dilutions of growth factors. Chronic viral infections, such as herpes simplex virus, Epstein-Barr virus (EBV), human immunodeficiency virus (HIV), papilloma virus, AIDS, chronic fatigue syndrome, Coxsackie B, hauta virus and hepatitis B virus, affect signal transduction mechanisms with deleterious effects within and between the host's immune and nervous systems. During chronic viral infection, host cell signal transduction and cell cycle regulation are altered, often causing cell injury and cell death.

Viruses lack the necessary biochemical machinery to manufacture proteins and must therefore insert their genetic material into a host cell genome in order to proliferate. Viruses consist of a protein coat and genetic material. RNA viruses additionally contain reverse transcriptase, an enzyme that translates the RNA into a DNA strand before insertion in the host cell genome.

During viral infection, the protein coat binds to the host cell's surface membrane enabling the virus' genetic information to subsequently enter the host cell. Entry occurs via various methods, one of which is attachment to specific membrane receptors, including growth factor receptors. For example, the cell receptors for the Epstein Barr and herpes simplex type 1 viruses have been identified as the third component of the complement receptor and the fibroblast growth factor receptor, respectively. Insertion of viral genetic information into the host cell's genome subverts the cell's normal metabolic and genetic mechanisms in order to prioritize viral gene expression and replication.

Chronic, or long-term, viral infections occur when the virus is able to overcome or effectively disrupt the normal neuronal and immunological defense mechanisms of the host. Several viruses, such as herpes simplex virus, EBV, human herpes 6 virus (HH6V), hepatitis B and HIV are able to cause latent (asymptomatic) infections in specific cell populations. Viral replication subsequently occurs in response to extracellular stimuli (Garcia-Blanco, M. A. and Cullen, B. R. 1991 Science 254:815–820). Infections become persistent when continuous viral replication occurs without substantial disruption of host cell function. Viral infections are terminated only when viral replication is disrupted.

Viral infection erodes feedback communication between the host's immune and nervous systems. For example, synthesis of adrenocorticotrophic hormone (ACTH) by lymphocytes after viral infection disrupts the normal feedback loop between pituitary/hypothalamus secretion of ACTH and the adrenal gland's synthesis of glucocorticoids in response to ACTH signals. Over-expression of ACTH causes increased expression of glucocorticoids which consequentially down-regulates the pituitary and suppresses the activities of T lymphocytes. This constant stress response often leads to extreme fatigue and exhaustion in patients with chronic viral infections. In an immune compromised patient, chronic infection leads to entry of virions into the bloodstream, the lymphatic vessels and/or the nerve pathways resulting in infection of new and distant cell populations.

DNA viral infections are often correlated with chronic or cancerous illnesses. For example, hepatitis B viral infection may be correlated with liver cirrhosis of the time and primary hepatocellular carcinoma 58% of the time compared to 17% in a control group. EBV infection correlates with Hodgkin's disease of the mixed cellularity type 60% of the time. Herpes type viral nucleic acid sequences from herpes simplex 1 and 2, cytomegalovirus and EBV have been found in the cerebrospinal fluid of patients with acute encephalitiso In addition, EBV has been found to induce receptors for human herpes 6 virus (HH6V). HH6V has, in turn, been found to be a cofactor in causing chronic fatigue syndrome and AIDS. The ability of viruses to cause cancer is contained within specific sequences of the viral genome. These sequences, known as oncogenes, have the ability to modulate gene transcription and regulation.

Gene transcription and regulation is modulated under normal conditions by growth factors. Growth factors are cell signalling polypeptides that bind to specific cell membrane receptors and initiate a cascade of intracellular events that affect cell proliferation and differentiation. As stated above, many growth factors bind to the same cell surface receptors as viruses and therefore activate the same metabolic pathways used by viral infected or transformed cells.

Growth factors and viruses use the same transcription sites to regulate cell proliferation. For example, TGFβ plays a critical role in the transmission of biological information by acting as an on/off switch that couples cell behavior to the external environment. Within the TGFβ promoter lies the proto-oncogene c-fos which codes for key transcription factors located at AP-1 transcription sites. Subversion of c-fos gene expression mediates HIV transcription and replication independent of control sites located at tat and NF$_k$β (Roebuck, K. A. et al. 1993 J. Clin. Invest. 92:1336–1348). Viral transcription in the human T-cell leukemia virus type 1 (HTLV-1), a virus with many characteristics similar to HIV, is tightly regulated by a Tax transactivator site located at the c-fos AP-1 site within the TGFβ promoter (Kim et al. 1990 J. Exp. Med. 172:121–129). When the TGFβ promoter is activated so is HTLV-1 Tax.

There are homologies between the gene sequences of growth factors, proto-oncogenes and oncogenes. It is now known that normal non-cancer cells contain proto-oncogenes that are homologous to the oncogenes found in some cancer causing viruses. These sequences have the power to regulate the cell cycle. Growth factors regulate the cell cycle by manipulating proto-oncogenes. Some proto-oncogene sequences are homologous with growth factors or their receptors. For example, the B chain of platelet-derived growth factor (PDGF) is homologous to the proto-oncogene c-sis (Doolittle, R. F., et al. 1983 Science 221:275–77). The receptor for epidermal growth factor (EGF) is homologous to the proto-oncogene c-erbβ (Downward, et al. 1984 Nature 307:521–527).

Chronic viral infections can lead to up-regulation of growth factor expression. For example, HIV infection up-regulates expression of tumor necrosis factor alpha (TNFα) and transforming growth factor beta (TGFβ). Overexpression of either of these growth factors disrupts normal transcriptional control of gene expression, leading to suppression of hematopoietic progenitor cells and increased HIV replication. TGFβ, secreted by HIV-infected lymphocytes, also promotes growth of Kaposi's sarcoma cells, fibroblasts and endothelial cells.

Specific hemopoietic growth factors have been used to treat diseases such as AIDS and cancer. Hemopoietic growth factors are logical immunomodulators to use in chronic viral infections and other diseases for several reasons. First, endogenous growth factors such as granulocyte-monocyte colony stimulating factor (GM-CSF) and macrophage colony stimulating factor (M-CSF) stimulate proliferation of hemopoietic progenitor cells. Second, lymphocytes, macrophages and natural killer cells that normally produce these factors are quantitatively and qualitatively defective after infection by HIV, HH6V or EBV. Third, primates infused with GM-CSF showed low toxicity with some positive but inconsistent rises in platelet number.

However, clinical studies on AIDS using GM-CSF and M-CSF at pharmacological doses (ug/kg/day) have produced mixed results. For example, injections or intravenous administration of GM-CSF at concentrations of 0.5–0.8 ug/kg/day transiently increased leukocyte, neutrophil, eosinophil and monocyte counts in AIDS patients with no significant rise in platelet counts or change in reticulocyte and lymphocyte counts (Miles, S. 1992 AIDS Res. Hum. Retroviruses 8:1073–1080). Subcutaneous injections of 0.25–4.0 ug/kg/day improved leukocyte counts with no improvement in hemoglobin or platelet counts. However, the side effects included increased HIV replication, increased levels of P24 antigen, chills, nausea, myalgia and flu-like symptoms (Poli, G. et al. 1991 J. Exp. Med. 173:589–597; Scadden, D. T. 1990 Hematopoietic Growth Factors in Trans. Med., Wiley-Liss Inc., New York, pp. 163–176). GM-CSF also occasionally caused thrombocytopenia. Granulocyte colony stimulating factor (G-CSF) has been effective in correcting neutropenia with some minor increases in lymphocyte counts. Additionally, hemoglobin and reticulocytes increased in numbers in patients given G-CSF alone or in combination with erythropoietin. However, resumption of treatment with AZT after use of these growth factors lead to severe anemia. Pharmacological doses of growth factors often have harsh side effects.

Homeopathy is founded on the principles of pharmacology except with much higher dilutions (much lower concentrations). Homeopathic medicine dates back to the nineteenth century. One of the basic tenets of homeopathic medicine is that a cure for a disease can be evoked by using a high dilution medicine that resembles but is different from the cause of the disease. Homeopathy is widely accepted as a useful therapeutic throughout Europe, the British Commonwealth countries and India, and has been demonstrated to have characteristic and reproducible effects. A critical review of more than 100 controlled and/or clinical studies of homeopathy determined that patients received positive healing benefits from homeopathy beyond the placebo effect (Kleijnen, J. et al. 1991 Brit. Med. J. 302:316–323).

Many homeopathic medicines are used at concentrations of micrograms ($10^{-6}$M) and nanograms ($10^{-12}$M); however, other homeopathic dilutions exceed Avogadro's number ($6.023\times10^{-23}$). When homeopathic compounds are diluted 1:10, with repeated successions (similar to vortexing) and repetitively diluted by this procedure at least 24 times a potency is achieved ($10^{-24}$) that contains essentially no molecules of the original substance. Homeopathic practitioners believe that the potency of a compound increases with increasing dilutions. The standard homeopathic dosage is 10–15 drops of a $10^{-12}$ molar, or 6C, solution administered three times per day. A 6C dilution approximates 1 ng/ml, which is used in cell culture but would be considered a lower than physiological dose when used orally.

Highly dilute homeopathic medicines have been effective in treating some viruses in vivo. Homeopathic dilutions of $1\times10^{-200}$ to $1\times10^{-1000}$ of typhoidinum, hydrophobinum, tuberculinum, nux vomica and malandrinum 100% inhibited pock-like lesions on the chorio-allantoic membrane of chicken embryos infected with a DNA virus, chicken embryo virus compared to controls (Singh, L. M. and Gupta, G. 1985 Brit. Homeopathy 74:168–174). Other homeopathic medicines, the same medicines at different homeopathic concentrations or control phosphate buffered solution (PBS), had lesser to no effect.

While the exact mechanism of action of homeopathic medicines is unknown, magnetic image resonance measurements on serial dilutions of substances indicate that the hydroxyl (OH) groups in the solvent of solutions continue to change as dilutions become successively higher (Sacks, A. D. 1983 J. Holistic Med. 5:175–176; Smith, R. and Boericke, G. 1968 J. Am. Inst. Homeopathy 61:197–212; Smith, R. and Boericke, G. 1966 J. Am. Inst. Homeopathy 59:263–279). It is clear that the specific effects of homeopathics are of a non-molecular origin, yet provide potent biological information that is clinically effective. It has been postulated that the effects of highly dilute compounds may use signal transduction pathways that are bioelectromagnetic in nature (Benveniste, J. 1993 Frontier Perspectives 3:13–15).

Bioelectromagnetics underlies biochemical reactions. The science of bioelectromagnetics studies the interactions of electromagnetic fields in living systems (Rubik, R. and Flower, R. G. 1993 Electromagnetic applications in medicine, NIH-OAM panel report to congress; Tenforde, T. S. and Kaune, W. T. 1987 Health Physics 53:585–606). Several studies on the effects of administering electromagnetic signals have been published. For example, Thomas et al. have demonstrated behavioral changes in rats following administration of a cyclotron electromagnetic field which resonates for the signal for unhydrated lithium ions (Thomas J. R. et al. 1986 Bioelectromagnetics 2:349–357). Researchers have also reported inhibition of tumor growth by administration of human interferon alpha (IFN-α) plus DC current (Sersa, G. and Miklavcic, D. 1990 Molecular Biotherapy 2:165–168).

Electromagnetic signals are believed to exert an effect at the cell membrane. Cell membranes maintain a carefully controlled surface potential that is measurable and reproducible. These potentials are transiently altered by electromagnetic fields or viral attachment, as well as by binding of neurotransmitters, hormones and growth factors. Electrical stimulation of cells temporally changes the cell's membrane potential and evokes consequential changes of RNA, DNA and protein synthesis (Bourguignon, G. J. and Bourguignon, L. Y. 1987 FASEB J. 1:398–402; Rodan, G. A. et al. 1978 Science 190:690–692).

Few effective treatments are available for disorders such as chronic viral infections, cancer and diabetes. Insulin-dependant diabetes, while regulated by insulin still has many systematic complications. Despite more than ten years of aggressive research, both conventional and naturopathic, no definitive treatment exists for HIV infection or acquired immunodeficiency syndrome (AIDS). There thus continues to be a need in the art for effective treatments for chronic viral infections, cancer and diabetes.

SUMMARY OF THE INVENTION

It is an object of the present invention to provide an effective treatment for disorders including chronic viral infections, cancer and diabetes which will slow the progression of disease and/or relieve disease symptoms. An additional objective is to provide such a treatment which does not lead to unwanted side effects. Another objective of the present invention is to provide such a treatment at a reasonable cost.

These and other objectives are achieved by administering homeopathic dilutions of growth factors, or electromagnetic signals corresponding to homeopathic dilutions of growth factors, to patients. In a preferred embodiment, the electromagnetic signals are radiofrequency signals.

Growth factors are cell signalling polypeptides which modulate cell proliferation and differentiation by binding to specific cell membrane receptors. Binding of growth factors to cell membrane receptors initiates a cascade of intracellular events that affect gene transcription and expression within the cell. Growth factors range in size from 3,500 to 250,000 daltons and, unlike hormones, generally act on nearby cells via autocrine and paracrine mechanisms. However, they may also act as second messengers for hormone signals. McDonald and Hendrickson have recently proposed a classification of growth factors into six superfamilies based on homology of three dimensional structure (1993 Cell 73:421–424). X-Ray crystallographic and NMR studies have shown that growth factors contain relatively few recurring structural folds despite their diversity. When structural folding is considered, several proteins previously regarded as hormones, such as insulin and growth hormone, are subsumed into the definition of growth factors. Cytokines and growth factors are very similar in both size and function. The term "growth factor" as used herein, therefore encompasses cytokines as well as the traditional growth factors.

A specific growth factor may have many cell sources and can use different signal transduction pathways at different times and with different cells. Growth factors are involved in complex feedback loops between the immune, nervous and endocrine systems.

The homeopathic dilutions of growth factors of the present invention are preferably of a concentration of less than about $10^{-6}$ molar, and preferably between about $10^{-6}$ molar and about $10^{-100,000}$ molar. The homeopathic dilutions may thus contain less than one molecule of growth factor. Homeopathic dilutions of growth factors are preferably administered orally, including in solid form, such as pellets or tablets.

Growth factors which may be utilized in the present invention include granulocyte macrophage-colony stimulating factor (GM-CSF), granulocyte-colony stimulating factor (G-CSF), macrophage-colony stimulating factor (M-CSF), tumor necrosis factor (TNFα), transforming growth factors (TGF), epidermal growth factors (EGF), stem cell factor (SCF) platelet-derived growth factors (PDGF), nerve growth factor (NGF), fibroblast growth factors (FGF), insulin-like growth factor (IGF), growth hormone, interleukin-1, interleukin-2, keratinocyte growth factor, ciliary neurotrophic growth factor, Schwann cell-derived growth factor, vaccinia virus growth factor, insulin, bombyxin, neu differentiation factor, v-Sis and glial growth factor/acetylcholine receptor-inducing activity.

Chronic viral infections that may be treated using the homeopathic dilutions of growth factors of the present invention include HIV, AIDS, EBV, herpes simplex, papilloma, cytomegalovirus, Coxsackie B, hauta virus, human herpes 6 virus and hepatitis B viral infections. Other disorders which may be effectively treated using the methods of the present invention include insulin-dependent and non-insulin dependent diabetes, and cancers such as leukemia and adenocarcinoma.

DETAILED DESCRIPTION

The homeopathic dilutions of the present invention typically comprise between $1 \times 10^{-6}$ and $1 \times 10^{-100,000}$ molar dilutions of growth factor in a pharmaceutically acceptable diluent. The preferred diluent is 100% grain alcohol. However, other diluents are known in the art and may be employed in the present invention. The homeopathic dilutions are preferably administered orally. In a preferred embodiment, homeopathic dilutions of growth factors are administered by means of pellets or tablets which retain the memory of the homeopathic dilution. These pellets are made from a suitable organic material, such as lactose (Botanical Labs., Bellingham, Wash.). Alternative methods of administration may also be used, such as intravenous delivery, injection and topical application.

Radiofrequency signals corresponding to homeopathic dilutions of growth factors may be administered as illustrated by the following examples, in which Example 1 describes a one time evaluation of homeopathic growth factor signals on HIV positive patients; Example 2 demonstrates the effect of repeated administrations of homeopathic growth factor signals on two HIV-positive patients; Example 3 describes the effects of administration of homeopathic growth factor signals to patients with Epstein-Barr viral infections (EBV); Example 4 describes the treatment of two cancer patients with signals corresponding to homeopathic growth factors and Example 5 demonstrates the effects of administration of homeopathic growth factor signals to two diabetic patients.

Figure 1A:
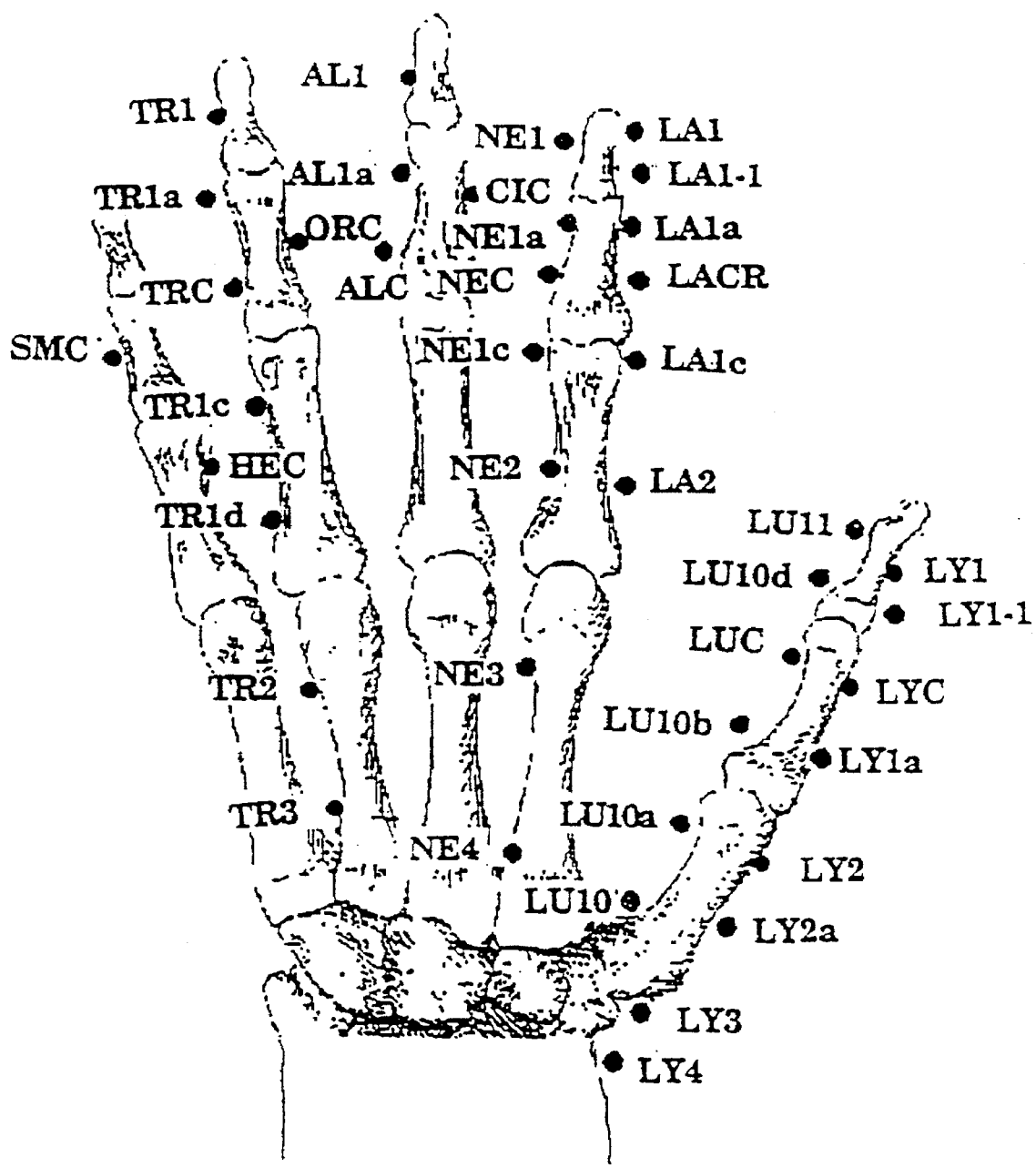
FIGS. 1A and B show electrical conductance points for the hand and foot as determined by Voll.
Figure 1B:
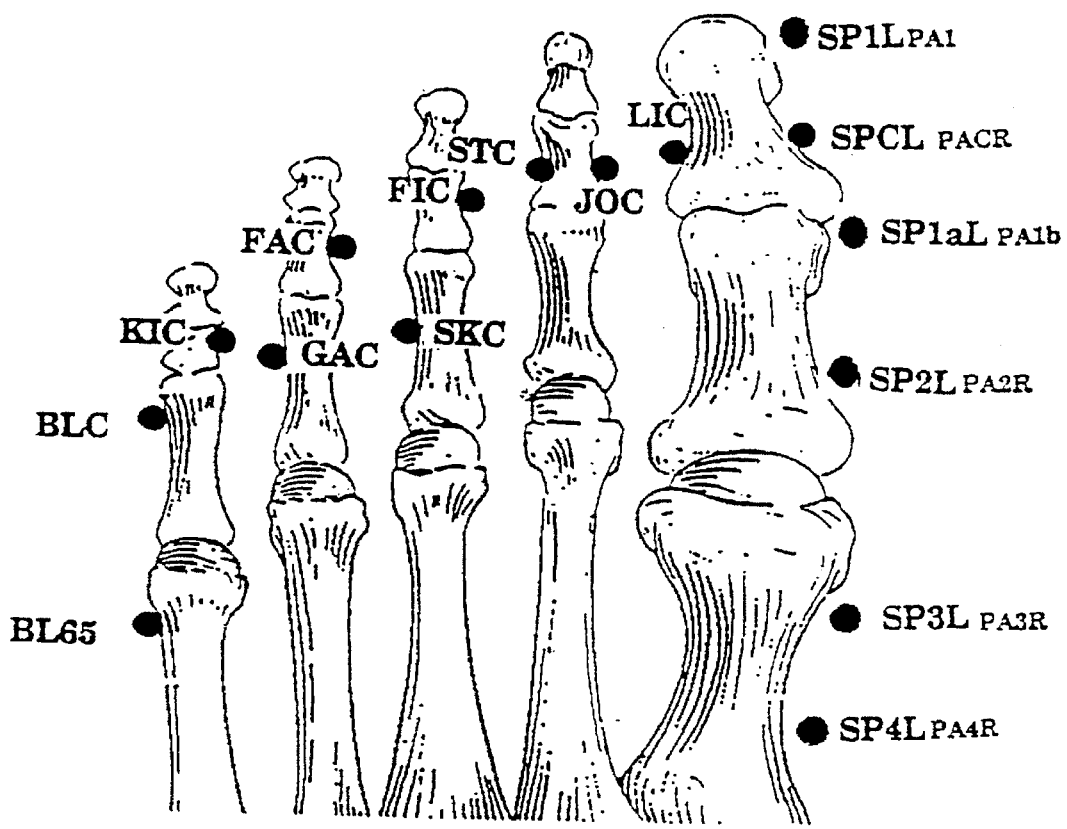

In all examples, patients were treated using the Life Information System TEN (LISTEN) (BioSource, Inc., Orem, Utah) which determines skin resistance or electrical conductance. The basic tenet behind the LISTEN system is that the points on the body normally referred to as "acupuncture points" have an optimal electrical resistance in healthy subjects which changes during illness. Each acupuncture point is associated with a specific meridian, or line of electrical conductance, which in turn is associated with a particular organ or system of the body (Voll, R. 1977 *Topographic positions of the measurement points in electro-acupuncture*. 1st English edition, H. Schuldt translator, Medizinish Literarische Verlagsgesellschaft mbH, C. Beckers Buchdruckerei GmbH & Co. KG, M. Sc. Uelzen, Germany, vols 1–4+supplement). FIGS. 1A and 1B illustrate hand and foot conductance points as defined by Voll. Points coded LY are related to lymph tissue, LU to lung tissue, LA to large intestine, NE to the nervous system, TR to neuroendocrine points, SP to spleen and PA to the pancreas.

By determining the electrical resistance at different points on a patient, it is possible to determine which organs are affected by a disease. In addition, a patient can be treated by providing a radiofrequency electrical signal which restores electrical conductance at specific points to normal levels.

The LISTEN system is a modified computer-based system which, in addition to determining electrical resistance at specific conductance points, can be used to administer radiofrequency signals corresponding to specific compounds, such as homeopathic dilutions of growth factors. These signals are generated by digital codes preprogrammed into the system by the manufacturer. The patient to be evaluated holds a source electrode, or brass bar, covered with wet sterile gauze in one hand. The practitioner holds a second brass electrode, or probe, like a pen and touches a specific conductance point in the other hand or in a foot with the probe while firmly supporting the finger or toe.

Conductance points are said to be approximately 3 mm in diameter and located in the epidermal layer of the skin, at the neck of the bones. In order to obtain the most accurate and reproducible measurement, the probe is placed at a 45° angle to the bone. Three tests are conducted per point in order to determine the reliability of the measurement.

Figure 2:
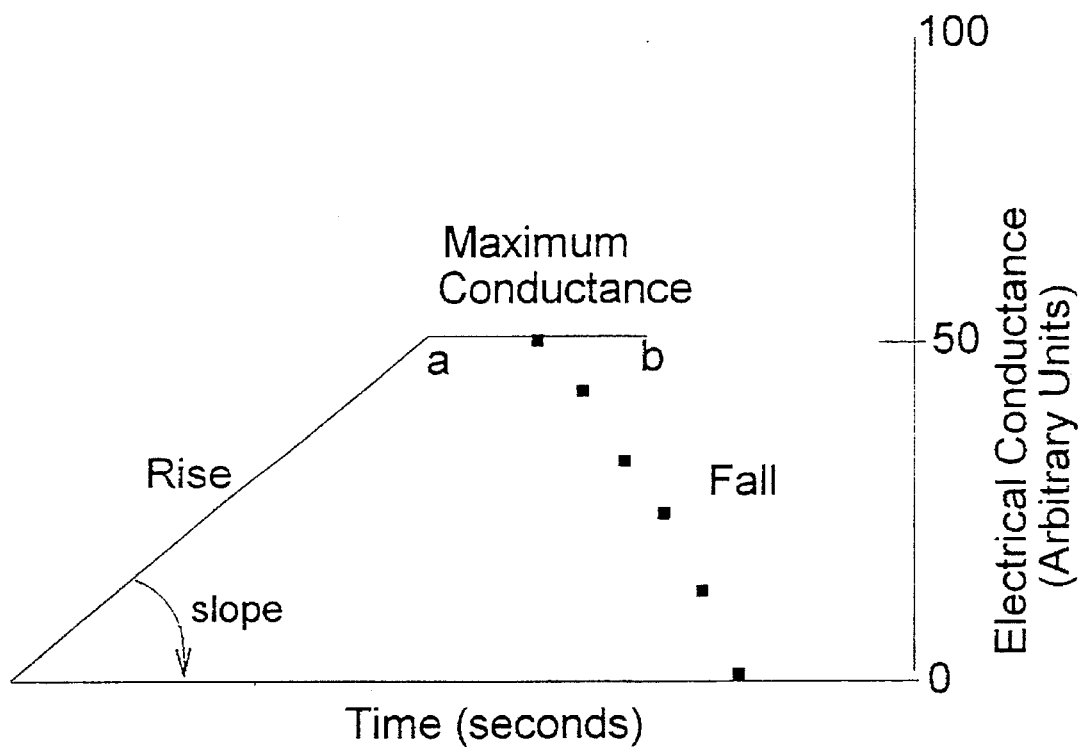
FIG. 2 shows the different outputs measured by the LISTEN system.

The LISTEN system determines three significant outputs: the rising slope; the maximal conductance; and the falling slope as shown in FIG. 2. The maximum is defined as the electrical conductance (mhos) produced at a patient's skin point in response to a maximal 5 volts signal. An internal clock calculates the time in seconds for the ohm meter to reach maximal conductance, and then during a constant one second period records the maximum and minimum conductance. The rising slope equals the maximum conductance divided by the seconds of time to reach maximum. The falling slope equals the maximum minus the minimum divided by seconds of time (in this case 1 second). Optimal resistance at an acupuncture skin point is 100,000 ohms (Zong-xiang 1981 Am. J. Acupuncture 9:203–216), scaled on this Y-axis at a value of 50 arbitrary units. Conductances in the range of 45–55 are thus indicative of a healthy, or disease-free, state. Calibration of the LISTEN device with a resistor occurs every six months so that 50 units=100,000 ohms with 1% precision. Preliminary studies on 28 points in 15 'healthy' individuals determined that the mean maximum conductance was 50.3±0.58 units (SEM) with a rise of 20.1±0.57 units/sec.

The general protocol followed in all the Examples is outlined below. Baseline conductance measurements were obtained on the right side plus one left side point for the spleen meridian in order to discover which points varied in their maximum and minimum from the optimal range of 45–55 and which points varied in rise from 14±0.3 and fall from 1.25±0.3. The areas in the body most out of balance were thus determined. The point with the highest abnormal reading or the highest point in the area with the greatest numbers of imbalanced energy was selected. The Specific Listings category of the LISTEN system was blind scanned in order to determine which growth factor was most likely to balance the specific point in terms of maximum-minimum readings and rise and fall readings. A radiofrequency signal corresponding to the selected growth factor was then administered to the patient for a period of one second to determine if it alone would balance the electrical conductance at the chosen point. All available growth factor signals were tested in this manner until it was determined which growth factor or combination of growth factors balanced all the points. If chronically low points could not be brought back into the normal range, a growth factor signal was selected which brought the conductance reading back close to normal. In the following examples, all points were brought back into the normal range.

Some patients in Table III were then challenged with radiofrequency signals corresponding to a variety of viruses. Each virus signal was tested for its ability to raise the patient's normal reading. Readings above 75 were considered to be a positive test. A signal corresponding to both the selected growth factor and the virus that stressed the normal point was subsequently administered to determine whether the selected growth factor could balance the electrical conductance under stress conditions.

EXAMPLE 1

Using the protocol outlined above, eleven HIV positive patients with CD4 counts in the range 67–570 were evaluated with the LISTEN system to determine whether electrical conductances could be balanced with growth factor signals. Electrical conductance was measured at points known to be weak in HIV and AIDS patients, including points corresponding to the spleen (SPCL), spleen lymphocytes homing to the upper body (SP1L), spleen lymphocytes homing to the lower body and gastrointestinal tract (SP2L), spleen blood filtering function (SP3L), environmentally related allergies (AL1R), general allergies (ALCR), lymph tissue of lungs (LY4R), lymph nodes (LY1R), general lymph function (LYCR), lymph drainage of tonsils/throat (LY1aR) and connective tissue (FICR).

Signals corresponding to growth factors at potencies of 6C (1:100 diluted six times=$10^{-12}$), 30C (1:100 diluted thirty times=$10^{-60}$), 200C (1:100 diluted 200 times=$10^{-400}$), 1000C (1:100 diluted 1000 times=$10^{-2000}$), or 1M, were administered.

The results of the study are shown in Table I, wherein the number of patients who responded to signals corresponding to different potencies of growth factors is indicated.

TABLE I

| | Appeared No. of People | 6C | 30C | 200C | 1000C |
|---|---|---|---|---|---|
| Nerve Growth Factor (NGF) | 7/11 | 3 | 2 | 1 | 4 |
| Insulin-like Growth Factor-1 (IGF$_1$) | 10/11 | 6 | 4 | 6 | 7 |
| Acidic Fibroblast Growth Factor ($\alpha$FGF) | 6/11 | 2 | 3 | 1 | 5 |
| Basic Fibroblast Growth Factor ($\beta$FGF) | 6/11 | 2 | 2 | 5 | 4 |
| BB Platelet-derived Growth Factor (BB-PDGF) | 9/11 | 3 | 5 | 1 | 5 |
| AA Platelet-derived Growth Factor (AA-PDGF) | 8/11 | 3 | 4 | 3 | 2 |
| AB Platelet-derived Growth Factor (AB-PDGF) | 7/11 | 3 | 5 | 3 | 4 |
| Transforming Growth Factor alpha (TGF$\alpha$) | 5/11 | 2 | 2 | 4 | 3 |
| Epidermal Growth Factor (EGF) | 5/11 | 0 | 2 | 2 | 3 |
| Stem Cell Factor (SCF) | 5/11 | 3 | 1 | 3 | 2 |
| Transforming Growth Factor-beta 1 (TGF$\beta$1) | 6/11 | 3 | 3 | 1 | 6 |
| Transforming Growth Factor-beta 2 (TGF$\beta$2) | 4/11 | 1 | 2 | 2 | 1 |
| Granulocyte-Macrophage Colony Stimulating Factor (GM-CSF) | 7/11 | 2 | 0 | 4 | 3 |
| Tumor Necrosis Factor alpha (TNF$\alpha$) | 7/11 | 4 | 2 | 4 | 4 |
| Macrophage Colony Stimulating Factor (M-CSF) | 7/11 | 2 | 2 | 2 | 4 |

In ten of the eleven patients, administration of insulin-like growth factor (IGF$_1$) signal brought the electrical conductance back into the normal range, with some patients responding to more than one dilution. BB Platelet-derived growth factor (BB-PDGF) and AA platelet-derived growth factor (AA-PDGF) were also highly effective in returning electrical conductance measurements to normal. Signals corresponding to higher dilutions of growth factors appeared to be more effective in restoring the electrical conductance to normal values.

In a separate study, an asymptomatic HIV-positive patient was given a simultaneous challenge of HIV infection using the LISTEN system while scanning dilutions specifically for $\beta$FGF to determine which dilutions between 6× and 6C might be useful. Signals corresponding to dilutions of 20×, 30×, 200×, 400×, 600×, 800× and 6C were found to bring the electrical conductances back into the normal range.

EXAMPLE 2

Two HIV-positive patients were treated with signals for homeopathic dilutions of growth factors using the LISTEN system several times per week for a period of three months using the protocol outlined above.

Peripheral blood lymphocyte counts were obtained for both patients at, or shortly after, the commencement of treatment with homeopathic growth factor signals and again at the end of the study. Prior to the commencement of treatment, both patients had a CD4 count of less than 200. Patient 2 was treated with homeopathic growth factor signals alone, while patient 1 was treated with a combination of homeopathic growth factor signals and, in addition, was treated therapeutically with homeopathic medicines and/or some botanicals corresponding to the digital codes from the LISTEN.

Signals of homeopathic growth factors corresponding to a combination of dilutions were administered for one second to points known to be weak in HIV and AIDS patients, as outlined in Example 1. Growth factors were selected based on their ability to effectively return conductance levels to normal. The number of times that signals corresponding to specific growth factors returned conductance levels to normal are shown in Table II.

TABLE II

| GROWTH FACTORS | NUMBER OF APPEARANCES | |
|---|---|---|
| | Patient One | Patient Two |
| Nreve Growth Factor (NGF) | 14 | 7 |
| Insulin-like Growth Factor-1 (IGF$_1$) | 4 | 8 |
| Acidic Fibroblast Growth Factor ($\alpha$FGF) | 13 | 6 |
| Basic Fibroblast Growth Factor ($\beta$FGF) | 4 | 0 |
| BB Platelet-derived Growth Factor (BB-PDGF) | 1 | 8 |
| AA Platelet-derived Growth Factor (AA-PDGF) | 5 | 0 |
| AB Platelet-derived Growth Factor (AB-PDGF) | 0 | 0 |
| Transforming Growth Factor alpha (TGF$\alpha$) | 10 | 0 |
| Epidermal Growth Factor (EGF) | 3 | 0 |
| Stem Cell Factor (SCF) | 5 | 0 |
| Transforming Growth Factor-beta 1 (TGF$\beta$1) | 5 | 0 |
| Transforming Growth Factor-beta 2 (TGF$\beta$2) | 0 | 2 |
| Granulocyte/Macrophage-Colony Stimulating Factor (GM-CSF) | 0 | 2 |
| Tumor Necrosis Factor alpha (TBF$\alpha$) | 0 | 0 |
| Macrophage-Colony Stimulating Factor (M-CSF) | 0 | 0 |

Nerve growth factor (NGF), acidic fibroblast growth factor ($\alpha$FGF) and transforming growth factor alpha (TGF$\alpha$) were most effective in bringing the electrical conductance measurements back into the normal range.

Figure 3A:
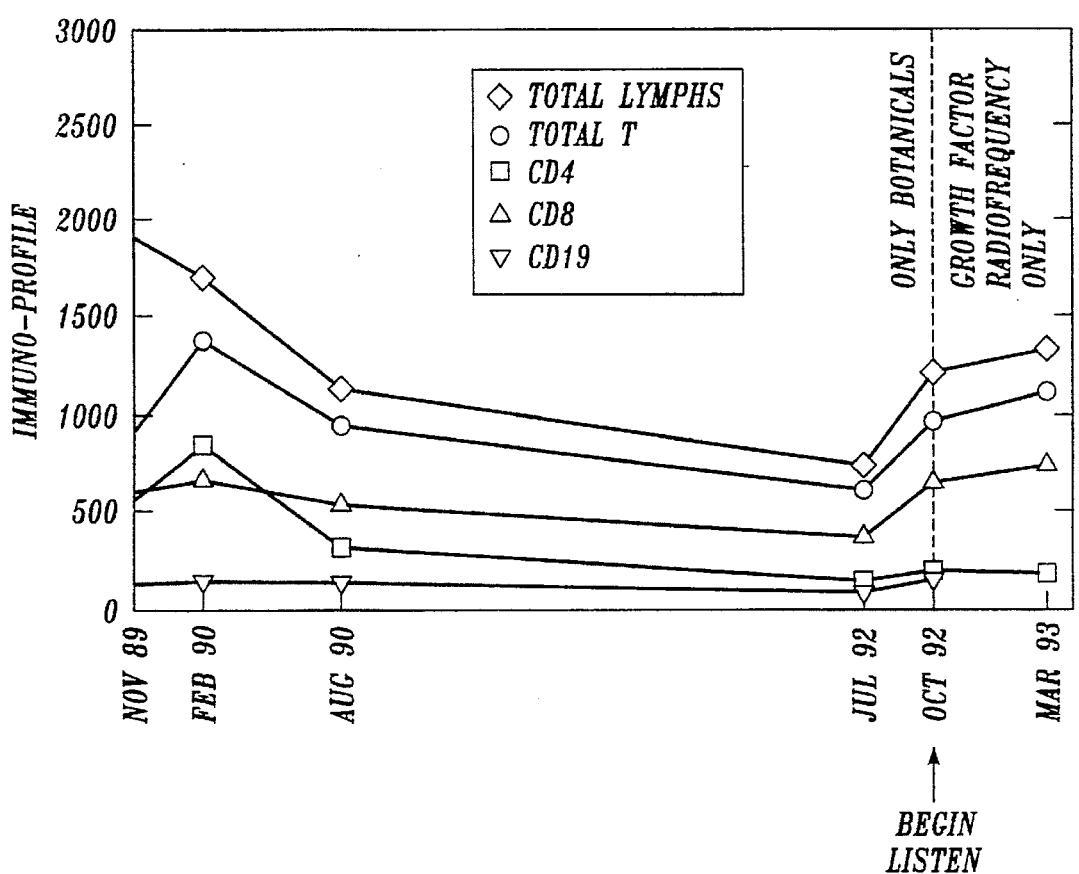
FIGS. 3A and B show the change in peripheral blood lymphocyte counts for two HIV-positive patients following treatment with homeopathic growth factor signals.

Prior to being treated with homeopathic growth factor signals, patient 2 had been treated with a variety of different botanicals. For the four-month period immediately prior to the commencement of homeopathic growth factor treatment, patient 2 was treated with the botanical bitter melon which resulted in increases in CD8, CD3, CD2 and CD19 counts of more than 50 percent. Bitter melon was then discontinued. As shown in FIG. 3A, administration of signals corresponding to homeopathic growth factors resulted in a slight increase in patient 2's peripheral blood lymphocyte counts without any other medical treatment. The average loss of CD4 cells in HIV-positive patients is 20% of the cells per year.

Figure 3B:
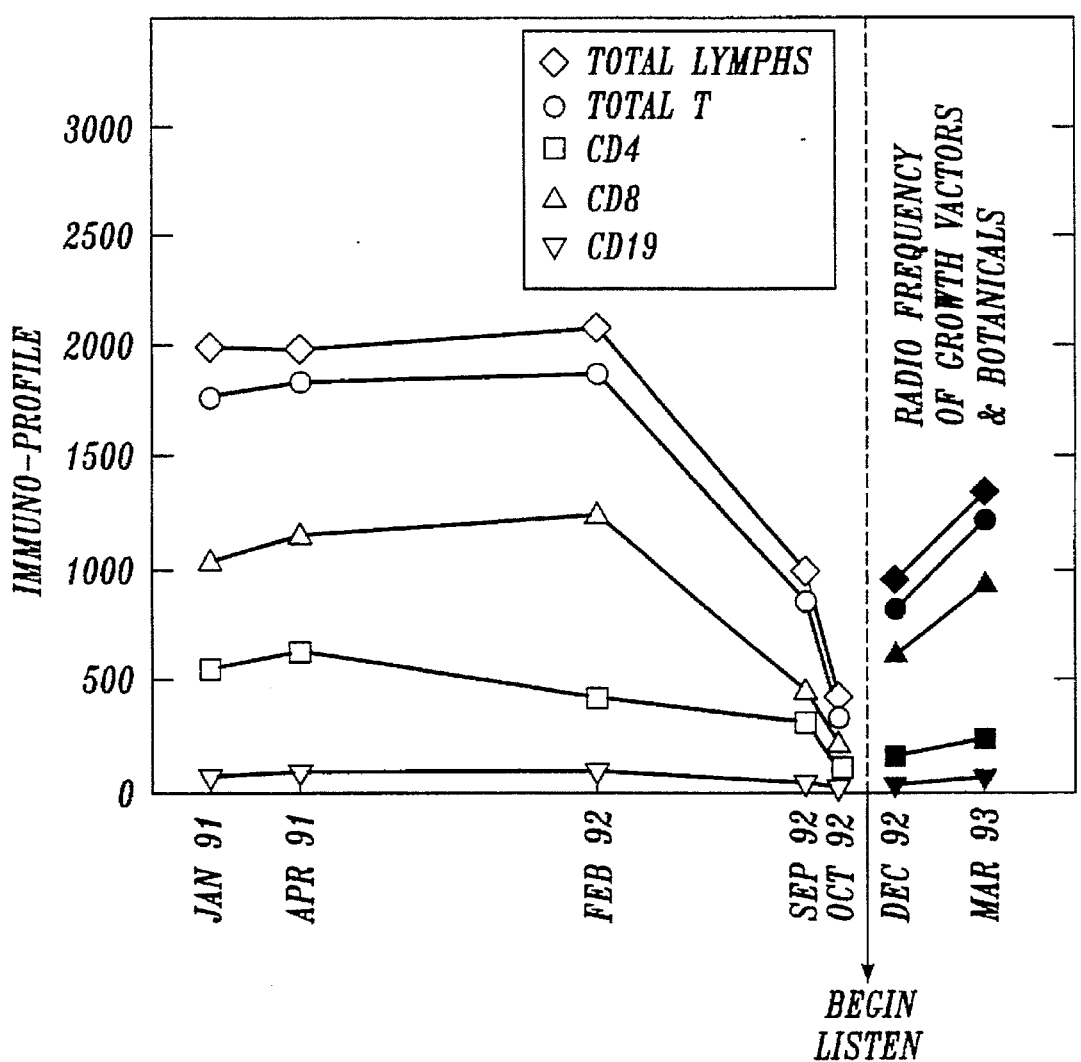

For patient 1, administration of signals corresponding to homeopathic dilutions of growth factors increased the CD4 count by 76%, while the CD8, CD2 and CD3 counts increased by 38%, as shown on FIG. 3B.

Figure 4:
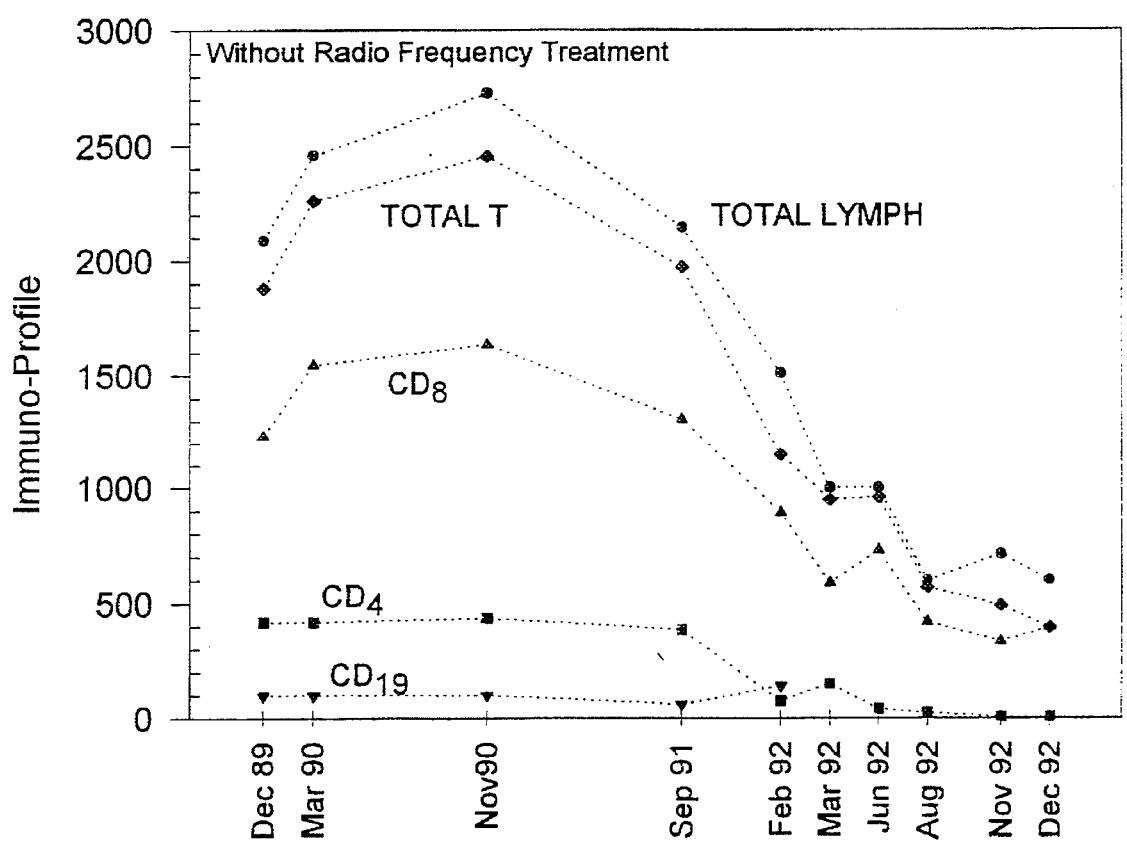
FIG. 4 shows the change in peripheral blood lymphocyte counts over time for a control HIV-positive patient.

These results are in marked contrast to the typical course of progression for HIV and AIDS in which the lymphocyte count continues to drop as the disease progresses. FIG. 4 shows the decrease in peripheral blood lymphocyte counts over time for a typical HIV-positive patient. This patient did not receive any homeopathic treatment, but did receive botanical supplements.

EXAMPLE 3

Figure 5:
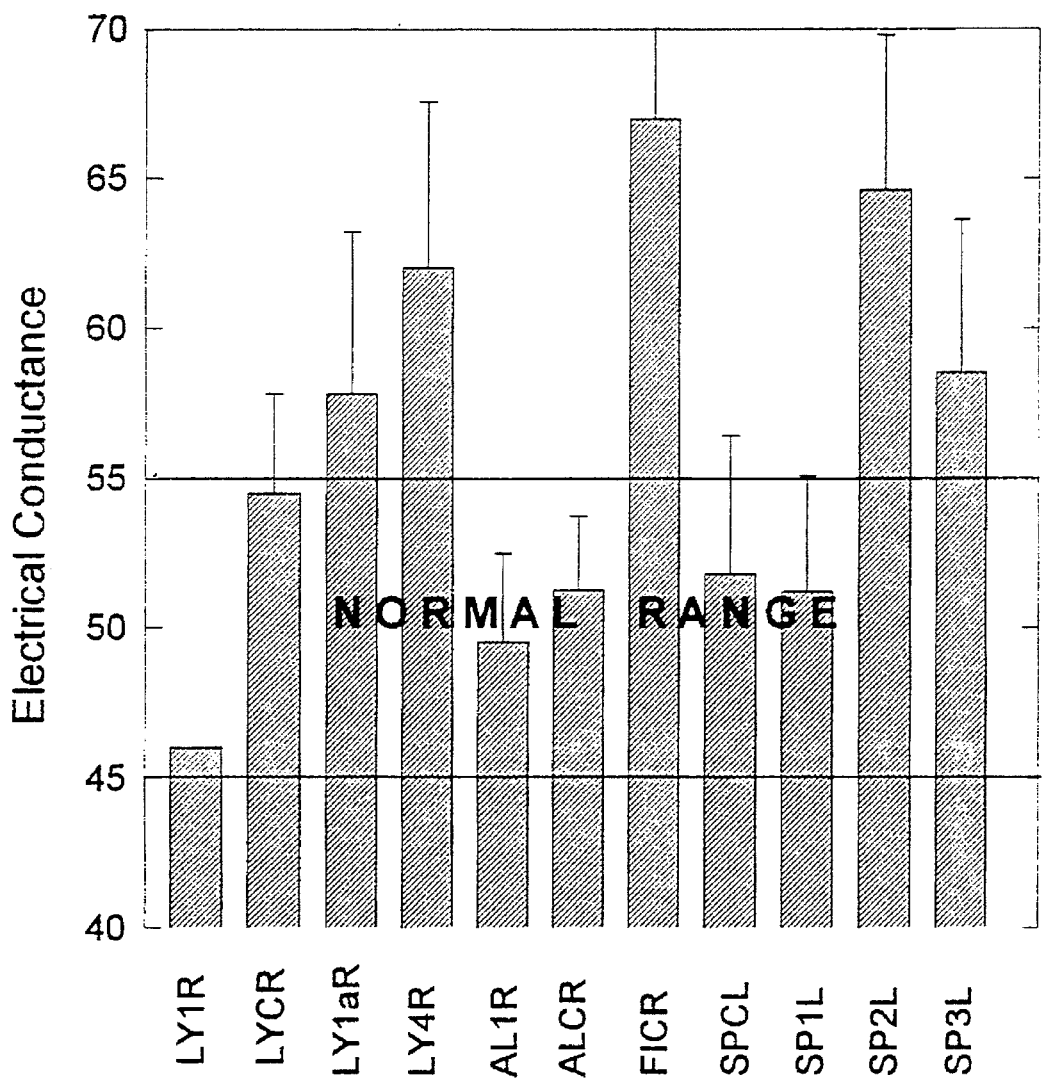
FIG. 5 shows the mean values of electrical conductances for fifteen patients with chronic EBV infection before treatment.

Electrical conductances of fifteen Epstein-Barr virus (EBV) patients were measured at acupuncture points for the immune system using the LISTEN system. The results are shown in FIG. 5. Higher than normal conductances were found at points corresponding to: lymph drainage of tonsils/throat (LY1aR) lymph tissue of lungs (LY4R); connective tissue (FICR); spleen lymphocytes homing to the lower body and gastrointestinal tract (SP2L); and spleen B lymphocytes and blood purification duties of spleen (SP3L). These results coincide with the clinical symptoms of patients with chronic EBV infection.

Figure 6:
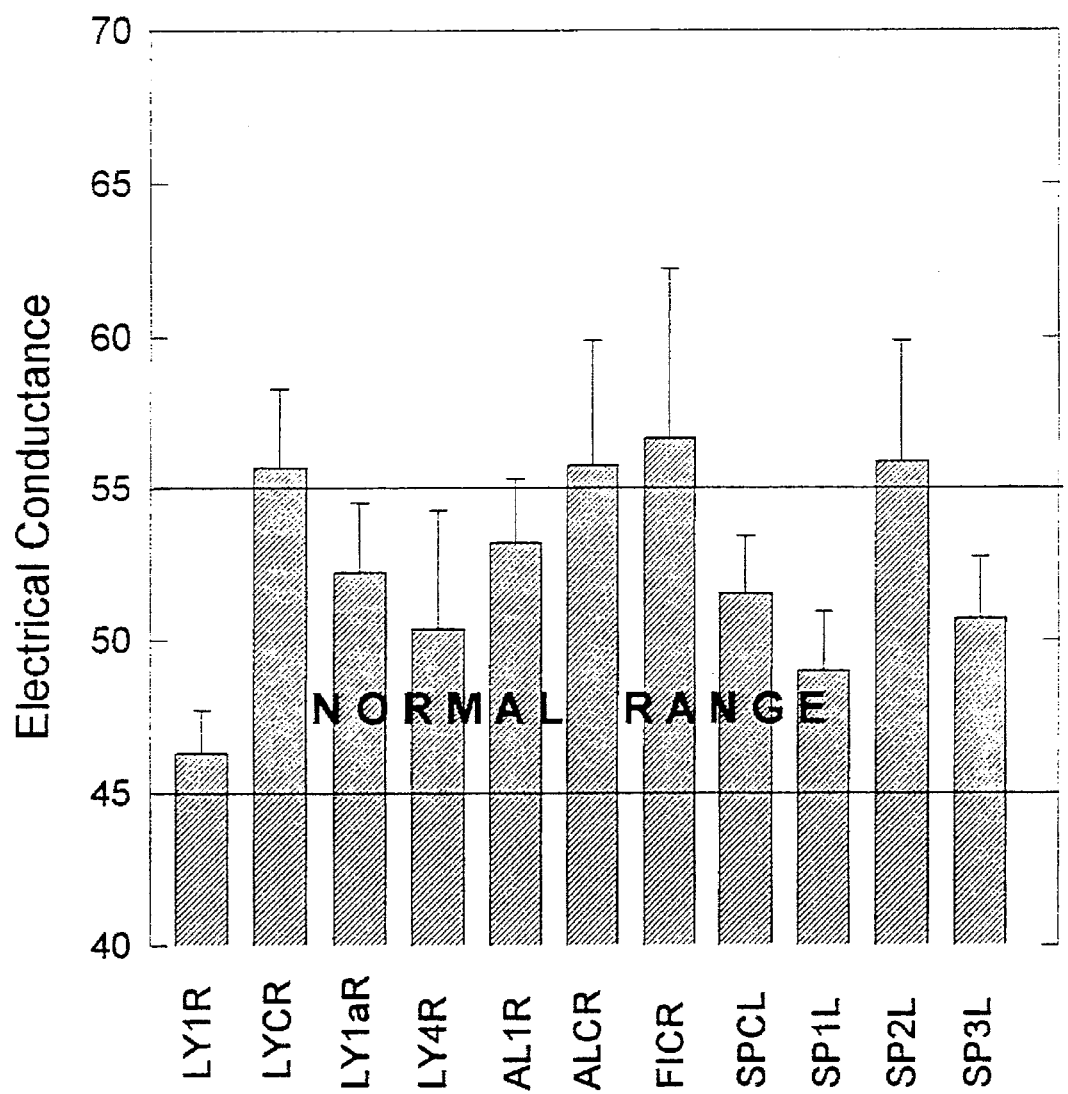
FIG. 6 shows the electrical conductances of eleven EBV patients after treatment with homeopathic growth factor signals and naturopathic supplements.

Eleven of the fifteen patients were subsequently treated for 3–9 months with a combination of homeopathic growth factor signals and botanicals corresponding to the LISTEN digital codes. Each patient was treated once per month using the previously outlined protocol. As shown in FIG. 6, significant improvement in electrical conductances occurred. Fewer clinical symptoms were also observed and reported by the patients. For example, the patients had less upper respiratory distress, less sore throats, more energy, fewer complaints regarding tendoniris, and somewhat improved digestion. These are all typical complaints of EBV patients.

Five of these patients were tested for the ability of signals corresponding to different dilutions of growth factors to normalize electrical conductances during one appointment. The results are shown in Table III.

TABLE III

| Patient | EBV Titers | Titer Levels | Growth Factor | Dilution |
|---|---|---|---|---|
| #1 | VCA IgG | 892 | AA PDGF | 6C |
| #2 | VCA IgG | 640 | AA PDGF | 800x, 30C |
|  | EA | 80 | BB PDGF | 800v, 6C |
|  | EBNA | pos | AB PDGF | 800x |
|  |  |  | TGFβ1 | 800x |
|  |  |  | TGFβ2 | 800x |
|  |  |  | TGFα | 800x |
|  |  |  | αFGF | 6C |
|  |  |  | IGF1 | 800x, 6C, 200C, 1000C |
| #3 | VCA IgG | 640 | Stem Cell Factor | 30C |
|  | EA | 80 |  |  |
|  | EBNA | neg |  |  |
| #4 | VCA IgG | 160 | AA PDGF | 6C |
|  | EA | 80 |  |  |
|  | EBNA | pos |  |  |
| #5 | VCA IgG | 1280 | IGF1 | 6C, 12C, 1000C |
|  | EA | neg | Insulin | 30C |
|  | EBNA | 40 | TGFβ1 | 600x, 6C, 1000C |
|  |  |  | βFGF | 6C, 1000C |
|  |  |  | TGFα | 30C, 1000C |
|  |  |  | NGF | 6C |
|  |  |  | Growth Hormone | 1000C |

As outlined above, a dilution of 6C is equal to 100 diluted six times ($10^{-12}$M). A dilution of 800× is equal to 1:10 diluted 800 times.

Prior to treatment, each of the five patients was tested for the presence of the following EBV titers: viral capsid antigen (VCA), early antigen (EA), and Epstein-Barr nuclear antigen (EBNA), as shown in Table III. In non-EBV infected subjects these titers are either negative or close to zero. Patient 1 was symptomatic with sore throat, sinus drainage and swollen glands at time of electrical conductance testing. Patients 2 and 5 were similar in that both had gall bladder surgery, hysterectomies, fibromyalgia, and were over forty and over-weight. Patient 2 also had chronic HPV and HSV infection. Patient 5's fasting blood sugar readings were indicative of mature onset of non-insulin dependent diabetes. Patient 3 additionally diagnosed as having multiple sclerosis. Patient 4 was additionally diagnosed as having rheumatoid arthritis.

All available growth factor signals were tested for patients 1 and 3–5. Based on the earlier HIV data, potentially useful growth factors were tested on patent 2 to determine effective dilutions, as shown in Table III.

Patient 5 was balanced on each of seven individual appointments using only growth factors. The growth factors were able to bring the electrical conductances into the normal range of 45–55 at every acupuncture point (over 30 points), often without additional supplementation with naturopathic medicines.

As described earlier all five patients demonstrated improved clinical symptoms. The growth factors found to be effective in treating these EBV patients included PDGF, TGFβ, αFGF, IGF1, NGF, insulin, growth hormone, and stem cell factor.

EXAMPLE 4

Two cancer patients were administered signals corresponding to homeopathic signals of growth factors using the standard LISTEN protocol. Patient 1 had chronic myeloid leukemia (CML), which is a stem cell disease in which stem cells fail to respond to physiologic feedback signals that regulate growth and differentiation of hematopoietic precursors. This patient had just begun treatment with alpha-interferon several hours before testing with the LISTEN system. Patient 2 had an adenocarcinoma (renal cell carcinoma) removed from her left side approximately 18 months prior to this study, and had metastases to the lung, skull and possibly to the bones and liver at the commencement of this study.

Figure 7:
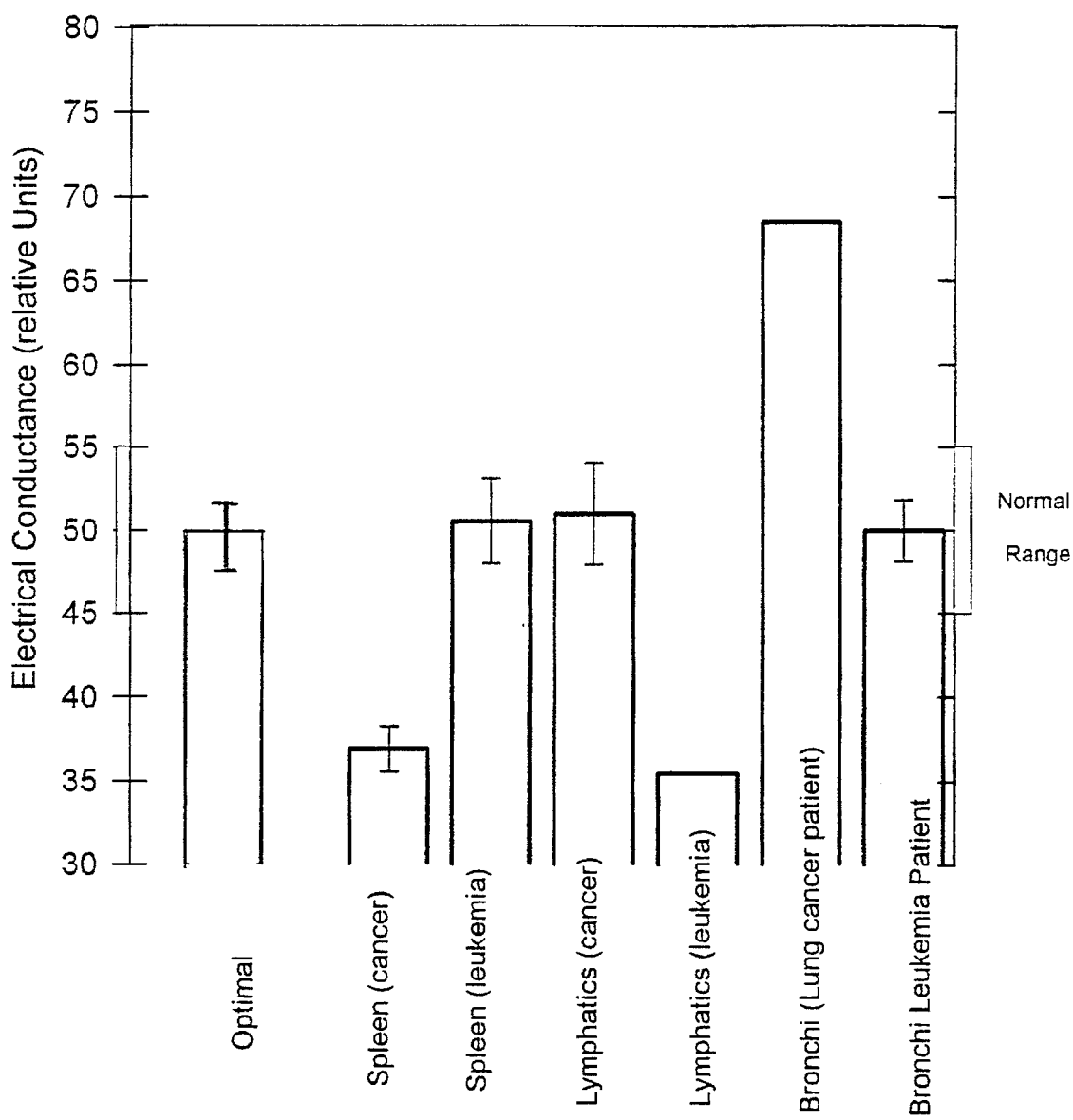
FIG. 7 shows the electrical conductances for two cancer patients prior to treatment with the LISTEN system.

As shown in FIG. 7, these two patients had significantly different electrical conductances. Both patients' electrical conductances were normalized by administration of specific homeopathic growth factor signals and naturopathic supplements. For patient 1, signals corresponding to combined dilutions of IGF1 were found to bring the conductances back into the normal range. For patient 2, signals corresponding to 30×, 100C and 1000C dilutions of NGF, an 8× dilution of AA PDGF, and 6C and 30C dilutions of TGFβ1 were found to be effective. The naturopathic supplements alone did not balance the electrical conductances. Patient 2, following treatment using the LISTEN system five times per week for one month, is no longer testing positive for cancer, using the serum AMAS™ test (Anti-Malignin Antibody in Serum determined with TARGET™ Reagent; Oncolab, Inc., Boston, Mass.). The specific results of the AMAS™ test are as follows: S-TAG 184 µg/ml (normal); F-TAG 79 µg/ml (normal); and net TAG 105 µg/ml (borderline). The results of blood chemistry analyses for Patient 2 before treatment and after treatment with signals corresponding to TGFβ1 are shown in Table IV.

TABLE IV

| Blood Chemistry | Before Treatment | After Treatment |
|---|---|---|
| Chemistry | | |
| Sodium | 139 meg/l | 143 |
| Potassium | 3.3 meg/l | 4.8 |
| Chloride | 100 meg/l | 108 |
| $CO_2$ | 25 meg/l | 23 |
| Glucose | 173 (high) mg/dl | 149 (high but closer to normal) |
| Calcium | 8.7 mg/dl | 9.0 |
| Bun | 18.0 mg/dl | 18.0 |
| Creatinine | 1.2 mg/dl | 1.2 |
| Bun/Creat. | 15.0 | 15.1 |
| Uric Acid | 5.5 mg/dl | 6.2 (high) |
| Cholesterol | 301 (high) mg/dl | 357 (high) |
| Triglycerides | 523 (high) | 305 (high but closer to normal) |
| Albumin | 4.0 g/dl | 4.1 |
| Globulin | 2.6 g/dl | 2.5 |
| A/G ratio | 1.5 | 1.6 |
| Total Bilirubin | 0.6 mg/dl | 0.4 |
| Direct Bilirubin | 0.4 mg/dl | 0.0 |
| Alkaline Phosphatase | 62 u/l | 108 |
| LDH | 136 u/l | 150 |
| AST (SGOT) | 8 u/l | 15 |
| ALT (SGPT) | 8 u/l | 18 |
| CBC | | |
| WBC | 7 × 1000/ul | 5.9 |

| Blood Chemistry | Before Treatment | After Treatment |
|---|---|---|
| RBC | 3.93 (Low) mil/ul | 4.49 (resolved) |
| Hemogloblin | 11.7 (Low) g/dl | 13.6 (resolved) |
| Hematocrit | 35.1 (Low) % | 41.7 (resolved) |
| MCV | 89.3 fl | 92.9 |
| MCH | 29.8 pg | 30.3 |
| MCHC | 33.3% | 32.6 |
| Neutrophils | 55.9% | 62.9% |
| Lymphocytes | 34.4% | 32.7% |
| Monocytes | 7.4% (monocytosis) | 2.4% (resolved) |
| Eosinophils | 1.4% | 1.2% |
| Basophils | 0.9% | 0.8% |
| Platelet count | 342,000/ul | 348,000/ul |

Prior to treatment, Patient 2 had anemia, as indicated by the hemoglobin, hematocrit and red blood cell count (RBC), and monocytosis, indicative of immune stress. Following treatment with radiofrequency signals corresponding to TGFβ1 for a period of one month, the patient's anemia and monocytosis had resolved. The patient's liver enzyme values (SGOT and SGPT) were also greatly improved, as was the alkaline phosphatase level.

EXAMPLE 5

Figure 8:
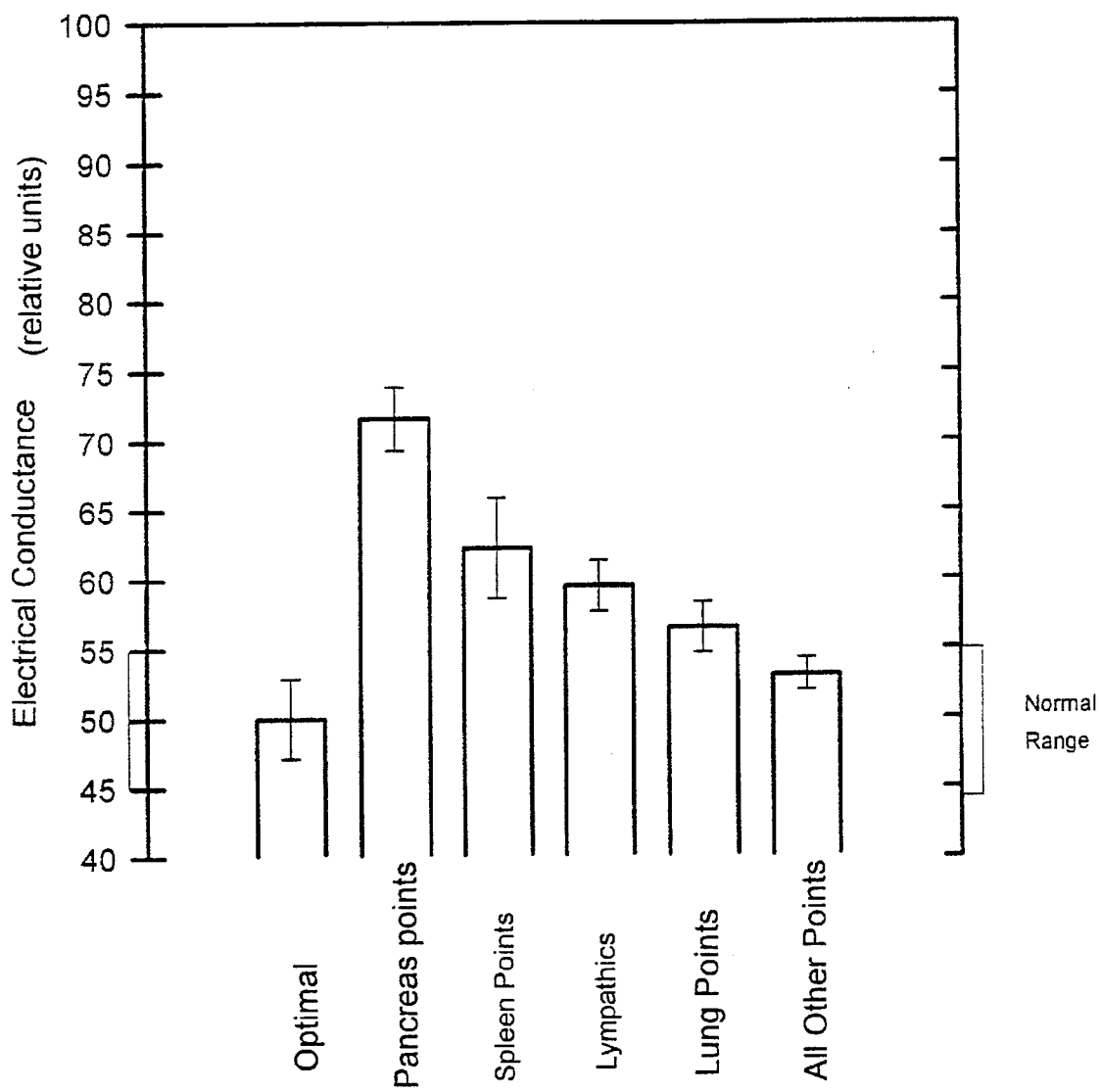
FIG. 8 shows the electrical conductances for two patients with insulin dependent diabetes prior to treatment with the LISTEN system.

A study was performed using the LISTEN system on two patients with insulin-dependent diabetes. Both patients were between 11 and 12 years of age and were treated within one year of onset of disease. Patient 1 serum-tested positive for Coxsackie B3 virus, which has been implicated through epidemiological studies to be a causative factor in the onset of diabetes. Patient 2 was not tested for Coxsackie B virus. The highly abnormal conductances of these patients shown in FIG. 8 were brought into the normal range by the administration of signals corresponding to naturopathic supplements plus a 6C dilution of insulin. On one occasion, patient 1's conductance points were completely balanced with signals corresponding to combined dilutions of stem cell factor or vasopressin without the need for additional signals of naturopathic supplements.

In a separate treatment session, all available signals for homeopathic growth factors were scanned to determine which signal would bring patient 2's conductances back to the normal range. A signal corresponding to a 600× dilution of βFGF was found to be most effective.

Although the present invention has been described in terms of specific embodiments, changes and modifications can be carried out without departing from the scope of the invention which is intended to be limited only by the scope of the appended claims.

I claim:

1. A method for treating a patient having a disorder selected from the group consisting of chronic viral infections, cancer and diabetes comprising administering a radio frequency signal selected to correspond to a dilution of less than about $10^{-6}$ molar of one or more growth factors at one or more skin conductance points.

2. A method for treating a patient having a disorder selected from the group consisting of chronic viral infections, cancer and diabetes as recited in claim 1, wherein said growth factor is selected from the group consisting of granulocyte macrophage-colony stimulating factor, granulocyte-colony stimulating factor, macrophage-colony stimulating factor, tumor necrosis factor, transforming growth factors, epidermal growth factors, stem cell factor, platelet-derived growth factors, nerve growth factors, fibroblast growth factors, insulin-like growth factor, growth hormone, interleukin-1, interleukin-2, keratinocyte growth factor, ciliary neurotrophic growth factor, Schwann cell-derived growth factor, vaccinia virus growth factor, insulin, bombyxin, neu differentiation factor, v-Sis and glial growth factor/acetylcholine receptor-inducing activity.

3. A method for treating a patient having a disorder selected from the group consisting of chronic viral infections, cancer and diabetes as recited in claim 1, wherein said radio frequency signal corresponds to a homeopathic dilution of between about $10^{-6}$ molar and about $10^{-100,000}$ molar.

4. A method as recited in claim 1, wherein the growth factor is granulocyte macrophage-colony stimulating factor.

5. A method as recited in claim 1, wherein the growth factor is transforming growth factor-beta.

6. A method as recited in claim 1, wherein the growth factor is insulin-like growth factor-1.

7. A method as recited in claim 1, wherein the growth factor is platelet-derived growth factor.

8. A method as recited in claim 1, additionally comprising obtaining a baseline conductance measurement at one or more conductance points in the patient to identify at least one abnormal conductance point prior to administering the radio frequency signal, and subsequently administering the radio frequency signal at an abnormal conductance point.

9. A method as recited in claim 1, additionally comprising administering multiple radio frequency signals corresponding to dilutions of a combination of growth factors to the patient.

10. A method as recited in claim 1, wherein the radio frequency signal is administered to the patient repeatedly.

11. A method for treating a patient having a disorder selected from the group consisting of chronic viral infections, cancer and diabetes as recited in claim 1 wherein said disorder is a chronic viral infection.

12. A method for treating a patient having a chronic viral infection as recited in claim 11, wherein said chronic viral infection is selected from the group consisting of herpes simplex, papilloma, cytomegalovirus, hepatitis B, Coxsackie B, hauta virus, and human herpes 6 virus.

13. A method for treating a patient having HIV, comprising administering a radio frequency signal selected to correspond to a dilution of less than about $10^{-6}$ molar of one or more growth factors.

14. A method for treating a patient having HIV as recited in claim 13, wherein said growth factor is selected from the group consisting of granulocyte macrophage-colony stimulating factor, granulocyte-colony stimulating factor, macrophage-colony stimulating factor, rumor necrosis factor, transforming growth factors, epidermal growth factors, stem cell factor, platelet-derived growth factors, nerve growth factors, fibroblast growth factors, insulin-like growth factor, growth hormone, interleukin-1, interleukin-2, keratinocyte growth factor, ciliary neurotrophic growth factor, Schwann cell-derived growth factor, vaccinia virus growth factor, insulin, bombyxin, neu differentiation factor, v-Sis and glial growth factor/acetylcholine receptor-inducing activity.

15. A method for treating a patient having HIV as recited in claim 14, wherein said radio frequency signal corresponds to a homeopathic dilution of between about $10^{-6}$ molar and about $10^{-100,000}$ molar.

16. A method for treating a patient having Epstein-Barr virus, comprising administering a radio frequency signal selected to correspond to a dilution of less than about $10^{-6}$ molar of one or more growth factors.

17. A method for treating a patient having Epstein-Barr virus as recited in claim 16, wherein said growth factor is selected from the group consisting of granulocyte macrophage-colony stimulating factor, granulocyte-colony stimulating factor, macrophage-colony stimulating factor, tumor necrosis factor, transforming growth factors, epidermal growth factors, stem cell factor, platelet-derived growth factors, nerve growth factors, fibroblast growth factors, insulin-like growth factor, growth hormone, interleukin-1, interleukin-2, keratinocyte growth factor, ciliary neurotrophic growth factor, Schwann cell-derived growth factor, vaccinia virus growth factor, insulin, bombyxin, neu differentiation factor, v-Sis and glial growth factor/acetylcholine receptor-inducing activity.

18. A method for treating a patient having Epstein-Barr virus as recited in claim 17, wherein said radio frequency signal corresponds to a homeopathic dilution of between about $10^{-6}$ molar and about $10^{-100,000}$ molar.

* * * * *